(12) United States Patent
Park et al.

(10) Patent No.: US 12,142,009 B2
(45) Date of Patent: Nov. 12, 2024

(54) GEOMETRIC CALIBRATION METHOD AND APPARATUS OF COMPUTER TOMOGRAPHY

(71) Applicant: 3D Industrial Imaging Co., Ltd., Seoul (KR)

(72) Inventors: Hyeonggyu Park, Seoul (KR); Kyunyun Kim, Anyang-si (KR)

(73) Assignee: 3D INDUSTRIAL IMAGING CO., LTD., Seoul (KR)

( * ) Notice: Subject to any disclaimer, the term of this patent is extended or adjusted under 35 U.S.C. 154(b) by 390 days.

(21) Appl. No.: 17/838,579

(22) Filed: Jun. 13, 2022

(65) Prior Publication Data
US 2022/0405970 A1    Dec. 22, 2022

(30) Foreign Application Priority Data
Jun. 21, 2021 (KR) .......................... 10-2021-0080024

(51) Int. Cl.
G06T 7/80    (2017.01)
G01T 7/00    (2006.01)

(52) U.S. Cl.
CPC ................ *G06T 7/80* (2017.01); *G01T 7/005* (2013.01); *G06T 2207/10081* (2013.01); *G06T 2207/20072* (2013.01); *G06T 2207/30204* (2013.01)

(58) Field of Classification Search
CPC ............. G06T 7/80; G06T 2207/10081; G06T 2207/20072; G06T 2207/30204;
(Continued)

(56) References Cited

U.S. PATENT DOCUMENTS

| 7,016,456 B2 | 3/2006 | Basu et al. |
| 7,147,373 B2 | 12/2006 | Cho et al. |

(Continued)

FOREIGN PATENT DOCUMENTS

| EP | 1760457 | 3/2007 |
| KR | 10-1027099 | 4/2011 |

(Continued)

OTHER PUBLICATIONS

Massimiliano Ferrucci et al., "Towards geometrical calibration of x-ray computed tomography systems—a review" Measurement Science and Technology 26.9 (Aug. 19, 2015): 092003.
(Continued)

*Primary Examiner* — Tsung Yin Tsai
(74) *Attorney, Agent, or Firm* — LEX IP MEISTER, PLLC (57) ABSTRACT

A geometric calibration apparatus detects points from projection regions onto which markers disposed on a phantom are projected, and calculates an output vector representing a probability distribution that gives a probability with which each point is a projection of each marker, by inputting data corresponding to each point to a learning model. The geometric calibration apparatus extracts a predetermined number of samples based on the probability distribution, obtains a candidate projection matrix by transforming correspondences between markers determined based on the samples among the markers and points determined based on the samples among the points, calculates points into which the markers are transformed by the candidate projection matrix, calculates a difference between a set of the transformed points and a set of the detected points, and designates the candidate projection matrix as a projection matrix when the difference is less than or equal to a threshold.

18 Claims, 9 Drawing Sheets

(58) Field of Classification Search
CPC ............. G06T 2211/441; G06T 11/005; G06T 2207/10072; G06T 5/80; G01T 7/005; A61B 6/583; A61B 6/584; A61B 6/4085; A61B 6/032; A61B 6/52; G06N 3/045; G06N 3/084; G06N 5/02; G06N 7/01; G06N 23/046; G06N 2223/419; G01N 2223/419

See application file for complete search history.

(56) References Cited

U.S. PATENT DOCUMENTS

| | | | |
|---|---|---|---|
| 7,844,094 B2 | 11/2010 | Jeung et al. | |
| 7,950,849 B2 | 5/2011 | Claus et al. | |
| 8,777,485 B2 | 7/2014 | Holt | |
| 9,572,539 B2* | 2/2017 | Carrat | A61B 6/12 |
| 10,311,602 B2* | 6/2019 | Choi | A61B 6/5205 |
| 10,478,147 B2 | 11/2019 | Hawker et al. | |
| 10,643,354 B2 | 5/2020 | Wang et al. | |
| 10,835,765 B2 | 11/2020 | Tulik et al. | |
| 11,110,301 B2* | 9/2021 | Yang | A61N 5/1081 |
| 2005/0117708 A1* | 6/2005 | Cho | A61B 6/027 378/164 |
| 2012/0259204 A1* | 10/2012 | Carrat | A61B 34/20 600/414 |
| 2015/0216498 A1* | 8/2015 | Schulze | A61B 6/584 378/207 |
| 2017/0238897 A1* | 8/2017 | Siewerdsen | A61B 6/466 |
| 2018/0197315 A1* | 7/2018 | Choi | A61B 6/4429 |
| 2020/0085404 A1* | 3/2020 | Siewerdsen | G06T 7/60 |

FOREIGN PATENT DOCUMENTS

| | | |
|---|---|---|
| KR | 10-1524937 | 6/2015 |
| KR | 10-2018-0082027 | 7/2018 |
| KR | 10-2018-0117323 | 10/2018 |
| KR | 10-2019-0123865 | 11/2019 |
| WO | 2016-148351 | 9/2016 |

OTHER PUBLICATIONS

Boris P. Selby et al., "Geometry calibration for x-ray equipment in radiation treatment devices and estimation of remaining patient alignment errors" Proc. SPIE 6913, Medical Imaging 2008: Physics of Medical Imaging. vol. 6913. SPIE (Mar. 2008).

Bernhard E. H. Claus, "Geometry calibration phantom design for 3D imaging" Proc. SPIE 6142, Medical Imaging 2006: Physics of Medical Imaging. vol. 6142 61422E (Feb. 28, 2006).

EPO, the extended European search report of the corresponding Application No. 22179761.6, dated Nov. 14, 2022.

Serge Belongie et al., "Shape context: A new descriptor for shape matching and object recognition", Advances in Neural Information Processing Systems 13, 831-837, 2000.

Pavlos S. Efraimidis et al., "Weighted random sampling with a reservoir", Information Processing Letters 97 (2006) 181-185, Dec. 2005.

Frederic Noo et al., "Analytic method based on identification of ellipse parameters for scanner calibration in cone-beam tomography" Physics in Medicine and Biology, vol. 45 (2000) 3489-3508, Nov. 2000.

Youngbin Cho et al., "Accurate technique for complete geometric calibration of cone-beam computed tomography systems" Medical Physics, vol. 32, No. 4, p. 968, Apr. 2005.

Xinhua Li et al., "A generic geometric calibration method for tomographic imaging systems with flat-panel detectors—A detailed implementation guide" Medical Physics, vol. 37, No. 7, p. 3844, Jul. 2010.

* cited by examiner

GEOMETRIC CALIBRATION METHOD AND APPARATUS OF COMPUTER TOMOGRAPHY

CROSS-REFERENCE TO RELATED APPLICATION

This application claims priority to and the benefit of Korean Patent Application No. 10-2021-0080024 filed in the Korean Intellectual Property Office on Jun. 21, 2021, the entire contents of which are incorporated herein by reference.

BACKGROUND

(a) Field

The present disclosure relates to a geometric calibration method and apparatus of computer tomography.

(b) Description of the Related Art

A computer tomography (CT) device, for example, a cone-beam CT (CBCT) device, acquires multiple X-ray images by imaging a subject with X-rays in different directions and creates a three-dimensional tomographic image from the X-ray images. Information on the directions in which X-ray imaging is performed is essential in order to generate an accurate tomographic image. An operation of specifying all imaging direction information of the CBCT device is called geometric calibration.

Geometric calibration methods of the CBCT device can be classified into a method using a geometric calibration phantom and a method using no geometric calibration phantom. The geometric calibration phantom refers to an object manufactured in a certain shape for the geometric calibration.

Some methods using some representative values as the imaging direction information of the CBCT device have been proposed for geometric calibration. These methods, however, obtain the imaging direction information by parameterizing some representative values, so projection matrices that fully represent the imaging direction information of the CBCT device cannot be obtained. In addition, although a geometric calibration method using phantom markers of different sizes has been proposed, manufacturing and verification of the phantoms are complicated because different types of phantom markers are used.

SUMMARY

Some embodiments may provide a geometric calibration method and apparatus capable of calculating accurate imaging direction information from an X-ray image of a phantom acquired by a computer tomography device.

According to one embodiment, there may be provided a geometric calibration apparatus including a memory configured to store one or more instructions and a processor configured to execute the one or more instructions. By executing the one or more instructions, the processor may detect a plurality of first points from a plurality of projection regions, respectively, a plurality of first markers disposed on a phantom being projected onto the projection regions in two dimensions by a computer tomography device, calculate an output vector representing a probability distribution that gives a probability with which each of the first points is a projection of each of the first markers, by inputting data corresponding to each of the first points to a learning model, extract a predetermined number of first samples based on the probability distribution, obtain a candidate projection matrix by transforming correspondences between second markers determined based on the first samples among the first markers and second points determined based on the first samples among the first points, calculate third points into which the first markers are transformed by the candidate projection matrix, calculate a difference between a first set of the third points and a second set of the first points, and designate the candidate projection matrix as a projection matrix in response to the difference being less than or equal to a threshold.

In some embodiments, the processor may transform each of the first points into a histogram. In this case, the data corresponding to each of the first points may be data obtained by being transformed into the histogram.

In some embodiments, the processor may extract the first samples by applying weighted random sampling to the probability distribution.

In some embodiments, the processor may extract a plurality of second samples for the first points, respectively, from a third set including indices of the first markers, and extract the first samples from a fourth set including indices of the first points such that a probability with which each element of the fourth set is extracted is a normalized value of a probability with which a first point corresponding to said each element among the first points is a projection of a marker at a second sample for the first point among the second samples.

In some embodiments, the processor may extract the first samples and the second samples using a weighted random sampling technique.

In some embodiments, the second markers may be markers that have, as indices, second samples, corresponding to the first samples among the second samples, among the first markers, and the second points may be points having the first samples as indices among the first points.

In some embodiments, in response to the difference being greater than the threshold, the processor may repeat a process of extracting the first samples, obtaining the candidate projection matrix, calculating the second points, and calculating the difference.

In some embodiments, the processor may calculate a minimum-weight perfect matching for a bipartite graph in which the first set and the second set are set as vertex sets and an edge between a vertex of the first set and a vertex of the second set has a weight, and calculate a sum of weights obtained by the minimum-weight perfect matching as the difference.

In some embodiments, the learning model may be a model that has been trained by using training data that have, as input data, data corresponding to fourth points into which the first markers are respectively transformed by a randomly-generated projection matrix and have, as correct answer labels, values indicating classification of the first markers.

In some embodiments, the data corresponding to the fourth points may be data obtained by transforming the fourth points into a histogram.

In some embodiments, the processor may apply direct linear transformation to the correspondences to obtain the candidate projection matrix.

According to another embodiment, a geometric calibration method of a computer tomography device may be provided. The geometric calibration method may include detecting a plurality of points $q'_j (j=1, \ldots, N')$ from a plurality of projection regions, respectively, a plurality of first markers disposed on a phantom being projected onto the projection regions in two dimensions by the computer tomography device, calculating an output vector $y_j=(P_{1j}, \ldots, P_{Mj})$ having, as elements, a probability $P_{ij}(i=1, \ldots, M)$ with which the $q'_j$ is a projection of each of the first markers, by inputting data corresponding to the $q'_j$ to a learning model, extracting samples $s'_k(k=1, \ldots, 6)$ from a set $\Omega'=\{1, \ldots, N'\}$ based on the $y_j$, obtaining a candidate projection matrix by transforming correspondences between second markers determined based on the samples $s'_k$ among the first markers and points determined based on the samples $s'_k$ among the $q'_j$, calculating points $\hat{q}_i$ into which the first markers are transformed by the candidate projection matrix, calculating a difference $d(\hat{Q}, Q')$ between a set $\hat{Q}=\{\hat{q}_1, \ldots, \hat{q}_i, \ldots, \hat{q}_M\}$ of the $\hat{q}_i$ and a set $Q'=\{q'_1, \ldots, q'_{N'}\}$ of the $q'_j$, and designating the candidate projection matrix as a projection matrix in response to the $d(\hat{Q}, Q')$ being less than or equal to a threshold.

In some embodiments, the geometric calibration method may further include transforming the $q'_j$ into a histogram. In this case, the data corresponding to the $q'_j$ may be data obtained by being transformed into the histogram.

In some embodiments, extracting the $s'_k$ may include extracting samples $s_j \in \Omega$ from a set $\Omega=\{1, \ldots, M\}$ such that a probability with which each element i of the set $\Omega$ is extracted for a given j is the $P_{ij}$, normalizing a probability $P_{s_j,j}$ at the $s_j$ into $\alpha P_{s_j,j}$, and extracting the $s'_k$ such that a probability with which each element j of the $\Omega'$ is extracted from the $\Omega'$ is $\alpha P_{s_j,j}$.

In some embodiments, the a may be a reciprocal of a sum of the $P_{s_j,j}$ at the $s_j$.

In some embodiments, calculating the $d(\hat{Q}, Q')$ may include calculating a minimum-weight perfect matching for a bipartite graph in which the $\hat{Q}$ and the $Q'$ are set as vertex sets and an edge between a vertex $\hat{q}_i$ of $\hat{Q}$ and a vertex $q'_j$ of $Q'$ has a weight $w_{ij}=\|\hat{q}_i-q'_j\|^2$, and calculating a sum of weights obtained by the minimum-weight perfect matching as the $d(\hat{Q}, Q')$.

In some embodiments, the geometric calibration method may further include, in response to the $d(\hat{Q}, Q')$ being greater than the threshold, repeating extracting the $s'_k$, obtaining the candidate projection matrix, calculating the $\hat{q}_i$, and calculating the $d(\hat{Q}, Q')$.

According to yet another embodiment, a computer program executed by a computing device and stored in a non-transitory recording medium may be provided. The computer program may cause the computing device to execute detecting a plurality of first points from a plurality of projection regions, respectively, a plurality of first markers disposed on a phantom being projected onto the projection regions in two dimensions by a computer tomography device, calculating an output vector representing a probability distribution that gives a probability with which each of the first points is a projection of each of the first markers, by inputting data corresponding to each of the first points to a learning model, extracting a predetermined number of first samples based on the probability distribution, obtaining a candidate projection matrix by transforming correspondences between second markers determined based on the first samples among the first markers and second points determined based on the first samples among the plurality of first points, calculating third points into which the first markers are transformed by the candidate projection matrix, calculating a difference between a first set of the third points and a second set of the first points, and designating the candidate projection matrix as a projection matrix in response to the difference being less than or equal to a threshold.

DETAILED DESCRIPTION OF THE EMBODIMENTS

In the following detailed description, only certain embodiments of the present invention have been shown and described, simply by way of illustration. As those skilled in the art would realize, the described embodiments may be modified in various different ways, all without departing from the spirit or scope of the present invention. Accordingly, the drawings and description are to be regarded as illustrative in nature and not restrictive. Like reference numerals designate like elements throughout the specification.

As used herein, a singular form may be intended to include a plural form as well, unless the explicit expression such as "one" or "single" is used.

In flowcharts described with reference to the drawings, the order of operations or steps may be changed, several operations or steps may be merged, a certain operation or step may be divided, and a specific operation or step may not be performed.

First, a principle of geometric calibration to be used in a geometric calibration method according to an embodiment of the present invention is described with reference to FIG. 1.

Figure 1:
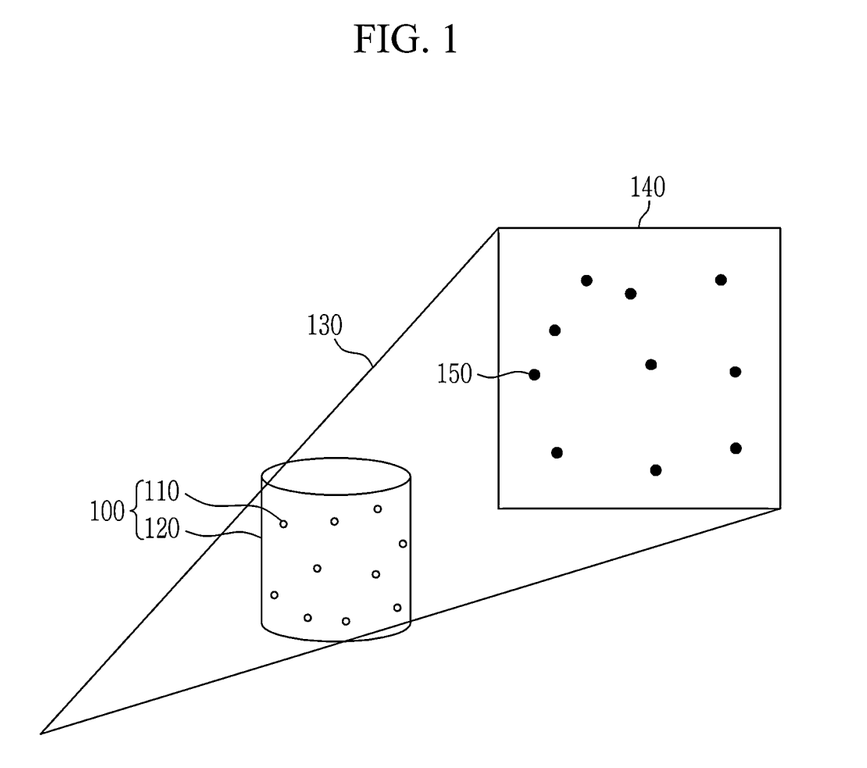
FIG. 1 is a drawing showing an example of a geometric calibration phantom according to an embodiment of the present invention.

FIG. 1 is a drawing showing an example of a geometric calibration phantom according to an embodiment of the present invention.

Referring to FIG. 1, a geometric calibration phantom 100 includes a plurality of phantom markers 110 and a main body 120 to which the markers 110 are fixed (or disposed). The markers 110 may include, for example, small balls having a radiopaque material (e.g., metal), and the main body 120 may include, for example, an object having a radiolucent material (e.g., acryl). When X-ray imaging 130 of the phantom 100 is performed, X-ray beams passing through the markers 110 are greatly attenuated compared to those that do not pass through the markers 110. As a result, when viewed from an X-ray image 140, regions onto which the markers 110 are projected are displayed with dark pixel values compared to their surroundings. Phantom-based geometric calibration can be regarded as a process of receiving a pattern 150 of these regions appearing in the two-dimensional X-ray image 140 and outputting geometric information about the X-ray imaging direction (hereinafter referred to as "X-ray imaging direction information").

The X-ray imaging direction information is mathematically expressed as a projection matrix. The projection matrix is given as a 3×4 matrix of real components, and can also be called a camera matrix. Geometrically, the projection matrix represents mapping or transformation from a set of three-dimensional points to a set of two-dimensional points. That is, when the three-dimensional point $p=(p_x, p_y, p_z) \in \mathbb{R}^3$ is given, this point is transformed as in Equation 1 by the projection matrix A.

$$\tilde{q} = A\tilde{p} \qquad \text{Equation 1}$$

In Equation 1, $\tilde{p}$ and $\tilde{q}$ are homogeneous coordinates of points p and q, respectively. Equation 1 is explicitly written as Equation 2.

$$\begin{bmatrix} \tilde{q}_u \\ \tilde{q}_v \\ \tilde{q}_w \end{bmatrix} = A \begin{bmatrix} p_x \\ p_y \\ p_z \\ 1 \end{bmatrix} \qquad \text{Equation 2}$$

By equation 2, the two-dimensional point $q \in \mathbb{R}^2$ is given as in Equation 3.

$$q = \begin{bmatrix} \tilde{q}_u/\tilde{q}_w \\ \tilde{q}_v/\tilde{q}_w \end{bmatrix} \qquad \text{Equation 3}$$

Accordingly, if the phantom marker $p=p_x, p_y, p_z$ is projected onto $q=(q_u, q_v)$ by the X-ray imaging, Equation 1 is expressed as in Equation 4 because the projection matrix A representing the X-ray imaging direction satisfies Equation 1.

$$A_{11}p_x + A_{12}p_y + A_{13}p_z + A_{14} = q_u \tilde{q}_w$$

$$A_{21}p_x + A_{22}p_y + A_{23}p_z + A_{24} = q_v \tilde{q}_w$$

$$A_{31}p_x + A_{32}p_y + A_{33}p_z + A_{34} = \tilde{q}_w \qquad \text{Equation 4}$$

In equation 4, $A_{ij} \in \mathbb{R}$ is an element in $i^{th}$ row and $j^{th}$ column of the 3×4 matrix A. Eliminating $\tilde{q}_w$ from Equation 4 gives Equation 5. That is, two equations for the projection matrix A can be obtained from the correspondence of $p \leftrightarrow q$.

$$P_x A_{11} + P_y A_{12} + p_z A_{13} + A_{14} - q_u(p_x A_{31} + p_y A_{32} + p_z A_{33} + A_{34})$$
$$= 0$$

$$P_x A_{21} + P_y A_{22} + p_z A_{23} + A_{24} - q_v(p_x A_{31} + p_y A_{32} + p_z A_{33} + A_{34})$$
$$= 0 \qquad \text{Equation 5}$$

If K correspondences $p^k \leftrightarrow q^k (k=1, \ldots, K)$ are given, 2K equations for the projection matrix A can be obtained from the K correspondences and given as in Equation 6 when expressed as a matrix equation.

$$\mathcal{M} a = 0 \qquad \text{Equation 6}$$

In Equation 6, a is a column vector of size 12, expressed as in Equation 7, and $\mathcal{M}$ is a matrix of size 2K×12 where a 2×12 partial matrix $\mathcal{M}_k$ corresponding to $(2k-1)^{th}$ and $2k^{th}$ rows is given as in Equation 8.

$$a = [A_{11} \; A_{12} \; A_{13} \; A_{14} \; A_{21} \; A_{22} \; A_{23} \; A_{24} \; A_{31} \; A_{32} \; A_{33} \; A_{34}] \qquad \text{Equation 7}$$

$$\mathcal{M}_k = \begin{bmatrix} p_x^k & p_y^k & p_z^k & 1 & 0 & 0 & 0 & 0 & -p_x^k q_u^k & -p_y^k q_u^k & -p_z^k q_u^k & -q_u^k \\ 0 & 0 & 0 & 0 & p_x^k & p_y^k & p_z^k & 1 & -p_x^k q_v^k & -p_y^k q_v^k & -p_z^k q_v^k & -q_v^k \end{bmatrix} \qquad \text{Equation 8}$$

From the above Equations, it can be observed that K must be equal to or greater than 6 (K≥6) in order to determine the solution a of Equation 6. The process of constructing the equation $\mathcal{M} a = 0$ from the correspondences $p^k \leftrightarrow q^k$ for the projection matrix A is called direct linear transformation (DLT).

One method for solving $\mathcal{M} a = 0$ obtained by the DLT with respect to the unknown a may use, for example, singular value decomposition (SVD). That is, if the matrix $\mathcal{M}$ is decomposed as in Equation 9 by applying the SVD to the matrix $\mathcal{M}$, a column of V corresponding to the smallest element among singular values appearing in diagonal matrix D becomes the solution of a. Rearranging a gives the projection matrix A.

$$\mathcal{M} = UDV^T \qquad \text{Equation 9}$$

In Equation 9, U is an orthogonal matrix obtained by eigenvalue decomposition of $AA^T$, V is an orthogonal matrix obtained by eigenvalue decomposition of $A^T A$, D is a diagonal matrix having the singular values as diagonal elements, and $A^T$ is a transpose matrix of A.

A geometric calibration phantom may be designed for a geometric calibration method according to various embodiments of the present invention. The geometric calibration phantom design may mean defining spatial positions of a plurality of markers constituting the phantom. As described above, in the geometric calibration phantom design, M (M≥6) markers (e.g., 110 in FIG. 1) may be disposed on a main body of the geometric calibration phantom (e.g., 110 in FIG. 1) to be positioned at three-dimensional coordinates $(p_1, \ldots, p_M)$. Here, M and $p_i$ (i=1, \ldots, M) may be values arbitrarily determined by a user. In some embodiments, the phantom may be determined based on the ease of fabrication or the size of a field of view in which the CBCT device can image. For example, as shown in Table 1, three-dimensional coordinates of 16 markers may be determined.

TABLE 1

| Marker positions | | |
|---|---|---|
| x | y | z |
| 11.131 | 29.021 | 62.179 |
| 9.851 | 11.078 | 84.876 |
| 28.609 | 58.157 | 11.798 |
| 26.290 | 89.173 | 59.756 |
| 36.147 | 64.311 | 86.668 |
| 76.712 | 20.840 | 2.826 |
| 56.729 | 1.279 | 35.583 |
| 87.399 | 54.607 | 2.605 |
| 38.432 | 86.550 | 12.123 |
| 10.308 | 51.591 | 61.399 |
| 49.733 | 37.451 | 98.660 |
| 18.009 | 67.792 | 47.432 |

TABLE 1-continued

| Marker positions | | |
|---|---|---|
| x | y | z |
| 15.280 | 25.564 | 1.724 |
| 44.632 | 95.417 | 11.597 |
| 12.424 | 73.945 | 57.123 |
| 74.076 | 89.189 | 78.380 |

Next, for a learning apparatus and a learning model according to various embodiments of the present invention are described with reference to FIG. 2 to FIG. 4.

Figure 2:
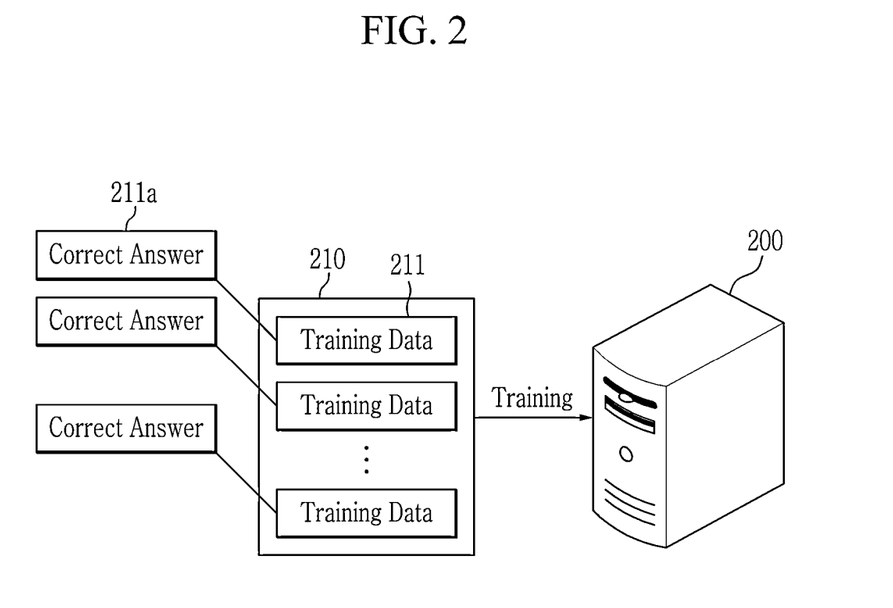
FIG. 2 is a drawing showing an example of a learning apparatus according to an embodiment of the present invention.
Figure 3:
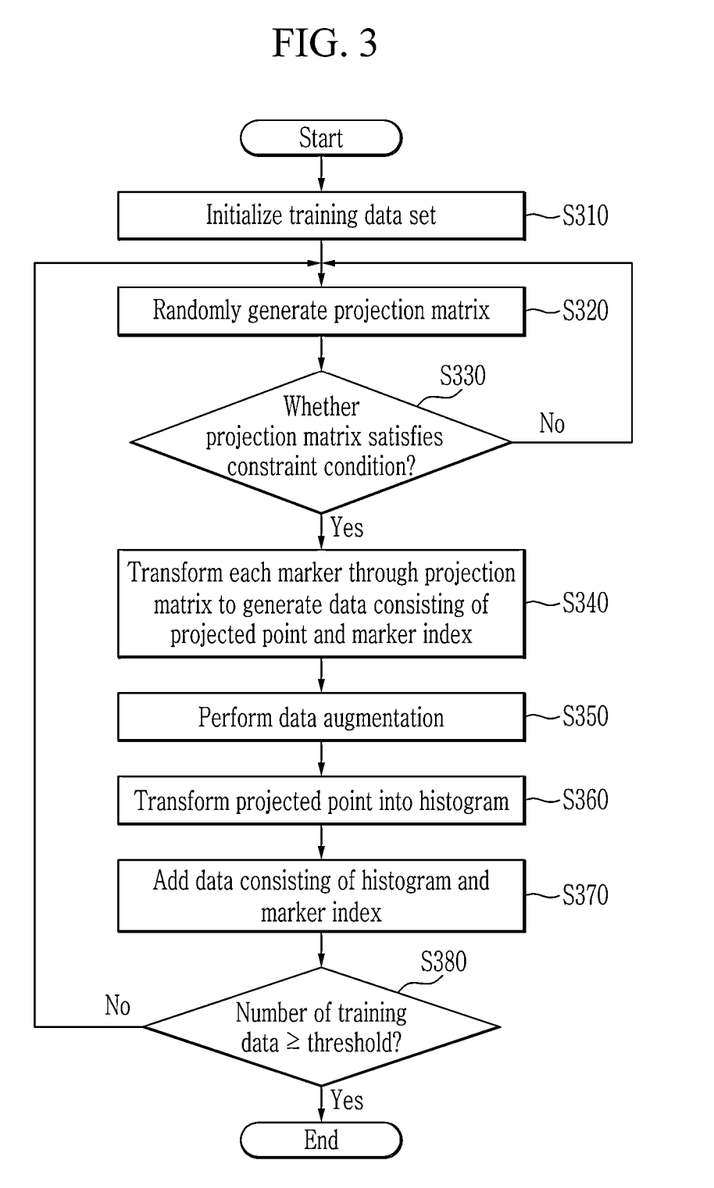
FIG. 3 is a flowchart showing an example of a training data generation method in a learning apparatus according to an embodiment of the present invention.
Figure 4:
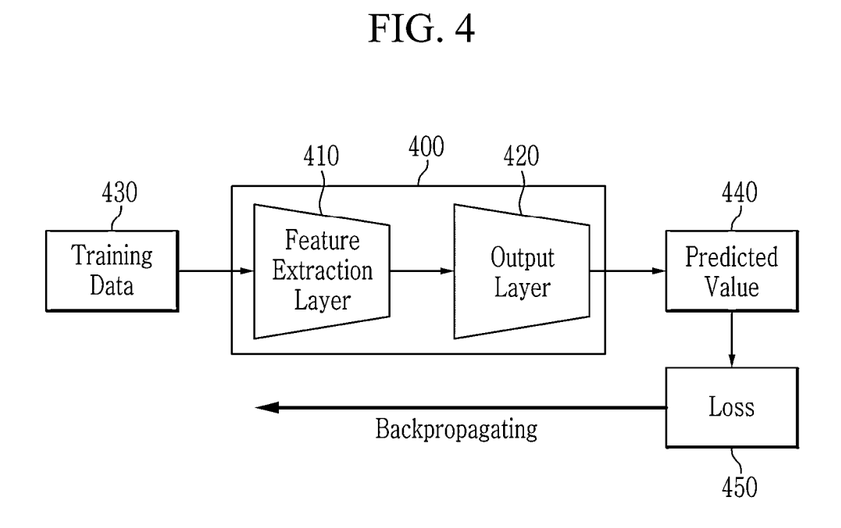
FIG. 4 is a drawing showing an example of a learning model or learning method in a learning apparatus according to an embodiment of the present invention.

FIG. 2 is a drawing showing an example of a learning apparatus according to an embodiment of the present invention, FIG. 3 is a flowchart showing an example of a training data generation method in a learning apparatus according to an embodiment of the present invention, and FIG. 4 is a drawing showing an example of a learning model or learning method in a learning apparatus according to an embodiment of the present invention.

Referring to FIG. 2, a learning apparatus 200 for geometric calibration is a computing device that performs machine learning on a neural network to generate a learning model that performs a target task. In some embodiments, the target task may include a task for geometric calibration. In some embodiments, the task for geometric calibration may be a task of finding a projection matrix.

In some embodiments, the learning model trained (generated) in the learning apparatus may be provided to a geometric calibration apparatus. The geometric calibration apparatus may perform geometric calibration based on the learning model. In some embodiments, the geometric calibration apparatus may be a computing device other than the learning apparatus. In some embodiments, the learning apparatus may perform functions of a geometric calibration apparatus.

In some embodiments, the computing device may be a desktop computer, a laptop computer, a server, or the like, but is not limited thereto and may be any kind of device having a computing function.

Although FIG. 2 shows the learning apparatus 200 is implemented as one computing device by way of example, in some embodiments, functions of the learning apparatus 200 may be implemented by a plurality of computing devices.

The learning apparatus 200 may train a neural network (e.g., a convolutional neural network, CNN) by using training data set 210 including a plurality of training data 211. Each training data 211 may include data in which a correct answer 211a is labeled. In some embodiments, the learning apparatus 200 may train the neural network by predicting a value by performing the target task by inputting the training data 211 to the neural network and backpropagating a loss between the predicted value and the correct answer 211a labeled in the training data to the neural network.

In some embodiments, the learning apparatus 200 may use a neural network learning model using a set of two-dimensional coordinates $Q=\{q_1, \ldots, q_N\}$ as the training data (i.e., inputs). In this case, a correct answer label of the training data may be a value indicating classification of a phantom marker in a geometric calibration phantom, for example, an index of the phantom marker.

Referring to FIG. 3, the learning apparatus first initializes the training data set D at S310. In some embodiments, the learning apparatus may initialize the training data set D to an empty set at S310. That is, $D \leftarrow \emptyset$.

The learning apparatus randomly generates twelve real numbers and creates a 3×4 projection matrix A having the twelve real numbers as elements at S320. The learning apparatus determines whether the projection matrix A satisfies a predetermined constraint condition at S330. In some embodiments, the predetermined constraint conditions may be set by a user configurable. In some embodiments, the predetermined constraint condition may include, for example, a condition that the projection matrix is a matrix that satisfies a specification of a designed pattern. That is, since there is no need to train the learning model with the projection matrix out of the specification, the constraint condition may be set in order to train the learning model only with the projection matrix that satisfies the specification. When the projection matrix A does not satisfy the predetermined constraint condition, the learning apparatus performs the process of S320 again.

When the projection matrix A satisfies the predetermined constraint condition, the learning apparatus transforms each phantom marker $p_i \in \mathbb{R}^3$ into $q_i \in \mathbb{R}^2$ through the projection matrix A at S340. In some embodiments, the learning apparatus may calculate a point $q_i$ to satisfy $\tilde{q}_i = A\tilde{p}_i$ as described with reference to Equation 1 at S340. Next, the learning apparatus designates as in $xf(q_1, \ldots, q_M)$, $y \rightarrow (1, \ldots, M)$ at S340. In some embodiments, the tuple x may be a set of two-dimensional coordinates of the points onto which the phantom markers are projected and correspond to data used as an input. The tuple y may correspond to data used as correct answer labels and be values indicating classification (e.g., indices) of the phantom markers.

In some embodiments, the learning apparatus may perform data augmentation on the training data at S350. The learning apparatus may generate augmented training data by changing x and y based on any one or a combination of two or more among various data augmentation techniques. In some embodiments, the learning apparatus may select any one or the combination of two or more among the various data augmentation techniques with a probability. In some embodiments, the various data augmentation techniques may include, for example, a technique of randomly selecting j to remove the j-th elements in x and y, a technique of randomly generating $q \in \mathbb{R}^2$ to add it as the last element of x and adding (N+1) as the last elements of y (N is the number of elements in each of x and y before the change), and a technique of randomly generating permutation σ and changing ordering of the elements in x and y according to the permutation σ. According to the third technique, it may be designated as in $xf(q_{\sigma(1)}, \ldots, q_{\sigma(N)})$, $yf(\sigma(1), \ldots, \sigma(N))$.

In some embodiments, the learning apparatus may transform each element of x obtained in the process of S340 or S350 into a histogram at S360. The x and y obtained in the process of S340 or S350 may be expressed as in $x = (x_1, \ldots, x_N)$, $y = (y_1, \ldots, y_N)$. The learning apparatus may transform each element of $x_j \in \mathbb{R}^2$ of x into the histogram $H_j = H(x_j; x)$ to facilitate training of a neural network model. The histogram transformation $H(x_j; x)$ may be defined in several ways to quantify spatial features of $x_j$ in relation to other points x. In some embodiments, the histogram transformation may be computed as in Equation 10 using shape context. Various histogram transformation techniques including, for example, "Shape context: A new descriptor for shape matching and object recognition" (Belongie, S. et al., The technique presented in Advances in neural information processing systems, 13, 831-837) may be used. The learning apparatus may transform x into the histogram by binding each element of Equation 10 and designating it as $Hf$ $(H_1, \ldots, H_N)$.

$$H_j(k) = \#\{j' \neq j : x_{j'} - x_j \in \text{bin}(k)\} \quad \text{Equation 10}$$

The learning apparatus adds N training data items consisting of $(H_j, y_j)$ generated in the process of S360 to the training data set at S370. That is, the learning apparatus may update the training data set D as in Equation 11.

$$D \leftarrow D \cup \{(H^1, y_1), \ldots, (H_N, y_N)\} \quad \text{Equation 11}$$

If sufficient training data items are added to the training data set at S380, the learning apparatus ends the generation of training data. If the sufficient training data items are not added, the learning apparatus repeats the process from S320. In some embodiments, the learning apparatus may determine that the sufficient training data items have been added when the number of elements (e.g., training data) of the training data set reaches a threshold.

Through these processes, the learning apparatus may generate the training data set D and store the generated training data set D in a storage device.

Next, referring to FIG. 4, a neural network 400 may include a learning model, and the learning model may include a feature extraction layer 410 and an output layer 420. In some embodiments, the learning model may be a multi-class classification model.

Two-dimensional input data (e.g., data transformed into a histogram) 430 of the training data is input to the feature extraction layer 410. The feature extraction layer 410 extracts features from the input data 430. Such the feature may be expressed in the form of a feature map.

In some embodiments, the feature extraction layer 410 may include a plurality of layers. A first layer among the plurality of layers may receive the input data and extract the feature map from the input data. The other layers may extract the feature map again from the feature map transferred by the previous layer and transfer it to the next layer. In some embodiments, each layer may extract the feature map by applying an operation of the corresponding layer to the input data or the input feature map. In some embodiments, the feature extraction layer 410 may include a convolution layer. The convolution layer may extract the feature map by applying a convolution filter to the input data or the input feature map.

In some embodiments, the feature extraction layer 410 may further include other layers such as a pooling layer and an activation layer. The pooling layer can extract features by performing a pooling operation on input features.

The output layer 420 predicts a predicted value 440 according to the target task based on the feature map extracted from the feature extraction layer 410. In some embodiments, the predicted value may be given as an M-dimensional vector y indicating values indicating classification (e.g., indices) of the phantom markers predicted by the target task.

In some embodiments, the output layer 420 may include a fully-connected layer that performs classification from the feature map output through the feature extraction layer 410. In some embodiments, a plurality of fully-connected layers may be provided.

A loss 450 between the predicted value 440 of the output layer 420 and a correct answer label of the input data may be calculated and be backpropagated to the neural network 400 so that the neural network 400 can be trained.

After repeatedly training the learning model using the training data of the training data set, the learning apparatus may store the learning model in the storage device. Next, the geometric calibration apparatus may perform geometric calibration by generating a projection matrix based on the learning model learned by the learning apparatus.

Next, a geometric calibration method according to various embodiments of the present invention is described with reference to FIG. 5 to FIG. 8.

Figure 5:
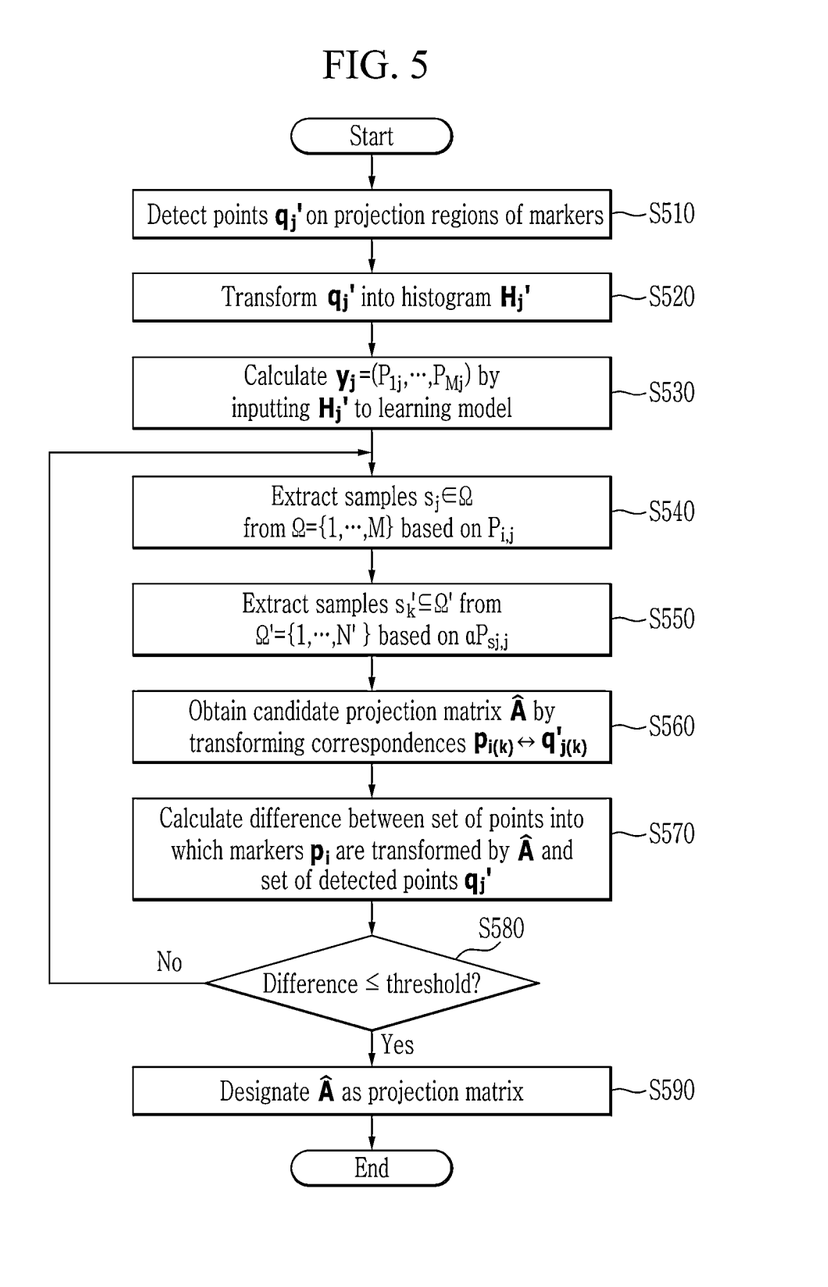
FIG. 5 is a flowchart showing an example of a geometric calibration method according to an embodiment of the present invention.
Figure 6:
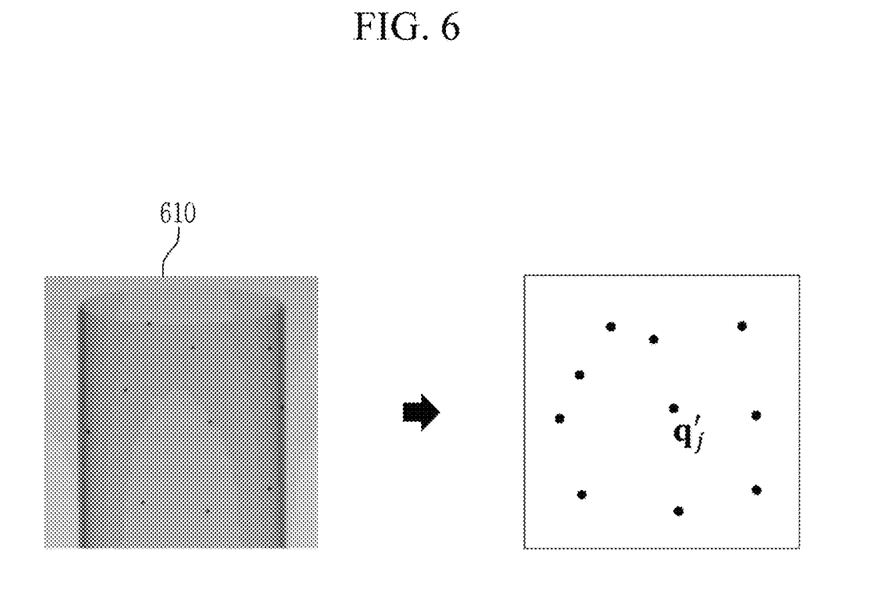
FIG. 6 is a drawing showing an example of detection of a marker projection region in a geometric calibration method according to an embodiment of the present invention.
Figure 7:
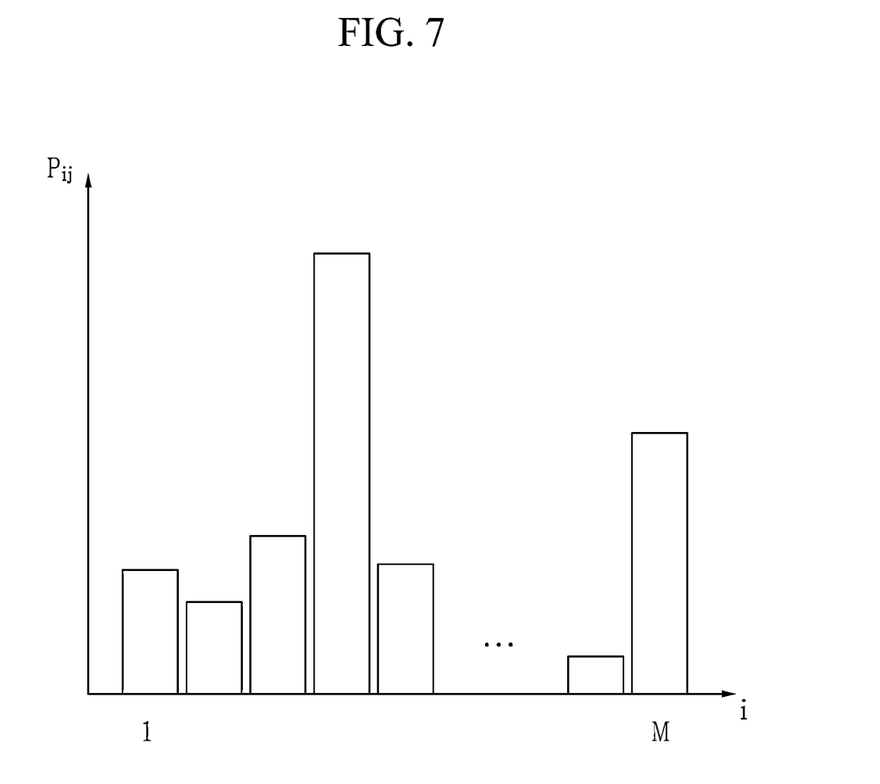
FIG. 7 is a drawing showing an example of a probability distribution in a geometric calibration method according to an embodiment of the present invention.
Figure 8:
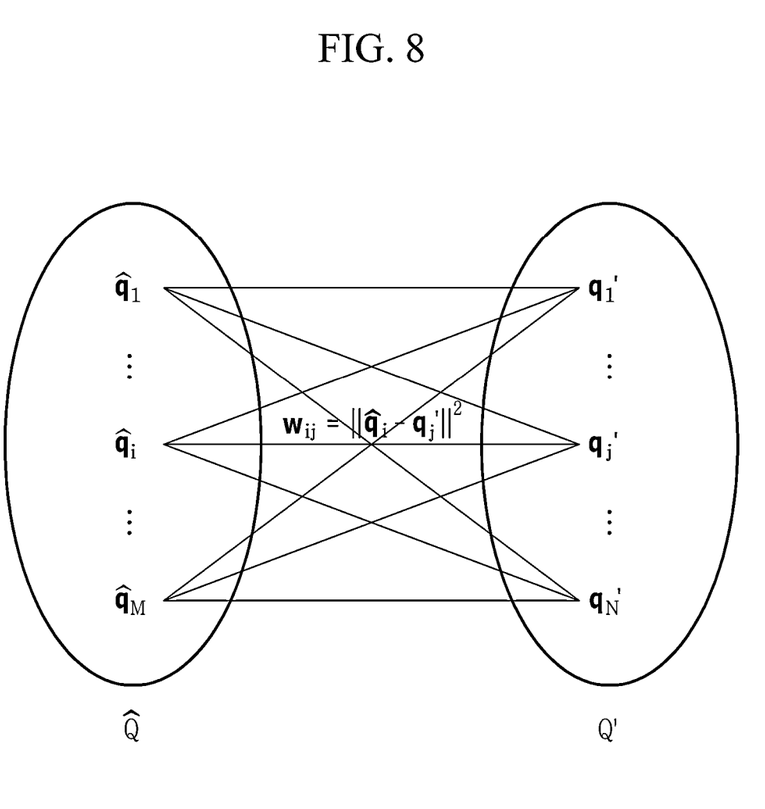
FIG. 8 is a drawing showing an example of a bipartite graph in the geometric calibration method according to an embodiment of the present invention.

FIG. 5 is a flowchart showing an example of a geometric calibration method according to an embodiment of the present invention, FIG. 6 is a drawing showing an example of detection of a marker projection region in a geometric calibration method according to an embodiment of the present invention, FIG. 7 is a drawing showing an example of a probability distribution in a geometric calibration method according to an embodiment of the present invention, and FIG. 8 is a drawing showing an example of a bipartite graph in the geometric calibration method according to an embodiment of the present invention.

A geometric calibration apparatus detects projection regions (e.g., 150 in FIG. 1) of markers (e.g., 110 in FIG. 1) in an X-ray image obtained by imaging a phantom (e.g., 100 in FIG. 1) by a CBCT device at S510. In some embodiments, the projection regions of the markers may appear as dark brightness values in the X-ray image. In some embodiments, the geometric calibration apparatus may detect the marker projection regions using a general digital image processing technique (e.g., a thresholding technique, etc.). The geometric calibration apparatus may designate the number of detected marker projection regions as N and a center point of each marker projection region as $q'_j \in \mathbb{R}$ (j=1, ..., N'). For example, as shown in FIG. 6, the geometric calibration apparatus may detect the center point $q'_j$ of each marker projection region in the X-ray image 610.

The geometric calibration apparatus transforms the detected point $q'_j$ and inputs data corresponding to the detected point $q'_j$ to the learning model at S520 and S530. In some embodiments, the geometric calibration apparatus may transform the detected point $q'_j$ into a histogram $H'_j$ at S520. In some embodiments, the geometric calibration apparatus may designate as in $xf(q'_1, \ldots, q'_{N'})$ and calculate the histogram $H'_j = H(q'_j; x)$, for example, based on Equation 10. The geometric calibration apparatus may calculate an output vector $y_j = (P_{1j}, \ldots, P_{Mj})$ by inputting the calculated histogram $H'_j$ to the learning model at S530. The geometric calibration apparatus may perform an operation of transforming the detected point $q'_j$ into the histogram $H'_j$ for each j(=1, ..., N') and calculating the output vector $y_j = (P_{1j}, \ldots, P_{Mj})$, for each j(=1, ..., N'), at S520 and S530.

When there is a set of two-dimensional points $\{q'_1, \ldots, q'_{N'}\}$, the output vector $y_j$ may be given as an M-dimensional vector $(P_{1j}, \ldots, P_{Mj})$ if the point $q'_j$ is transformed into the histogram and input to the learning model. Here, $P_{ij}$ (i=1, ..., M) means a probability with which the point $q'_j$ is a projection of the phantom marker $p_i$. The output vector $y_j$ may be expressed as, for example, a probability distribution as shown in FIG. 7. Accordingly, the geometric calibration apparatus may estimate, based on the probability distribution $y_j$, which of the phantom markers $p_1, \ldots, p_M$ generates each of the detected points $q'_1, \ldots, q'_{N'}$. The geometric calibration apparatus may extract six samples (referred to as "first samples") based on the probability distribution $y_j$ at S540 and S550. In some embodiments, the geometric calibration apparatus may extract the sample by applying a weighted random sampling technique to the probability distribution. Various weighted random sampling techniques including, for example, the technique presented in "Weighted random sampling with a reservoir" (Efraimidis, P. et al., Information Processing Letters, 97 5, 181-185) may be used.

In some embodiments, the geometric calibration apparatus may extract samples $s_j \in \Omega$ (referred to as "second samples") from a set $\Omega=\{1, \ldots, M\}$ such that a probability with which each element i of the set $\Omega$ is extracted for a given j is a probability $P_{ij}$. In some embodiments, the geometric calibration apparatus may extract the sample $s_j$ using the weighted random sampling technique in order to achieve sampling according to the probability distribution. In this case, the geometric calibration apparatus may perform an operation of extracting the sample $s_j$ for each j (=1, ..., N'). For example, when M=9 and N'=9, the samples $s_j$ may be extracted as shown in Table 2. In some embodiments, the weighted random sampling technique may allow the samples $s_j$ of a different pattern to be extracted the next time the sample $s_j$ is extracted.

TABLE 2

| i | j = 1 | j = 2 | j = 3 | j = 4 | j = 5 | j = 6 | j = 7 | j = 8 | j = 9 |
|---|---|---|---|---|---|---|---|---|---|
| 1 | $P_{11}$ | $P_{12}$ | $P_{13}$ | $P_{14}$ | $P_{15}$ | $P_{16}$ | $P_{17}$ | $P_{18}$ | $P_{19}$ |
| 2 | $P_{21}$ | $P_{22}$ | $P_{23}$ | $P_{24}$ | $P_{25}$ | $P_{26}$ | $P_{27}$ | $P_{28}$ | $P_{29}$ |
| 3 | $P_{31}$ | $P_{32}$ | $P_{33}$ | $P_{34}$ | $P_{35}$ | $P_{36}$ | $P_{37}$ | $P_{38}$ | $P_{39}$ |
| 4 | $P_{41}$ | $P_{42}$ | $P_{43}$ | $P_{44}$ | $P_{45}$ | $P_{46}$ | $P_{47}$ | $P_{48}$ | $P_{49}$ |
| 5 | $P_{51}$ | $P_{52}$ | $P_{53}$ | $P_{54}$ | $P_{55}$ | $P_{56}$ | $P_{57}$ | $P_{58}$ | $P_{59}$ |
| 6 | $P_{61}$ | $P_{62}$ | $P_{63}$ | $P_{64}$ | $P_{65}$ | $P_{66}$ | $P_{67}$ | $P_{68}$ | $P_{69}$ |
| 7 | $P_{71}$ | $P_{72}$ | $P_{73}$ | $P_{74}$ | $P_{75}$ | $P_{76}$ | $P_{77}$ | $P_{78}$ | $P_{79}$ |
| 8 | $P_{81}$ | $P_{82}$ | $P_{83}$ | $P_{84}$ | $P_{85}$ | $P_{86}$ | $P_{87}$ | $P_{88}$ | $P_{89}$ |
| 9 | $P_{91}$ | $P_{92}$ | $P_{93}$ | $P_{94}$ | $P_{95}$ | $P_{96}$ | $P_{97}$ | $P_{98}$ | $P_{99}$ |
| | $s_1 = 6$ | $s_2 = 3$ | $s_3 = 8$ | $s_4 = 1$ | $s_5 = 4$ | $s_6 = 9$ | $s_7 = 7$ | $s_8 = 2$ | $s_9 = 5$ |

Next, the geometric calibration apparatus may extract samples $\{s'_1, \ldots, s'_6\} \subseteq \Omega'$ through sampling without replacement such that a probability with which each element j of a set $\Omega'=\{1, \ldots, N'\}$ is extracted from the set $\Omega'$ is $\alpha P_{s_j,j}$ at S550. For example, the sample $s'_k$ may be extracted as shown in Table 3 based on the example of Table 2. That is, the geometric calibration apparatus may extract the samples $\{s'_1, \ldots, s'_6\}$ of size 6. In some embodiments, the geometric calibration apparatus may use a weighted random sampling technique to extract the samples $s'_k$ (k=1, ..., 6). In some embodiments, the probability $\alpha P_{s_j,j}$ may be a probability into which the probability $P_{s_j,j}$ at the sample $s_j$ (i.e., the probability with which the point $q'_j$ is a projection of the marker at $s_j$) is normalized. In some embodiments, $\alpha$ denotes a normalization constant which may be given, for example, as a reciprocal of a sum of the probabilities at the samples $s_j$ as in Equation 12.

TABLE 3

| j | $s_j$ | P |
|---|---|---|
| 1 | 6 | $\alpha P_{61}$ |
| 2 | 3 | $\alpha P_{32}$ |
| 3 | 8 | $\alpha P_{83}$ |
| 4 | 1 | $\alpha P_{14}$ |
| 5 | 4 | $\alpha P_{45}$ |
| 6 | 9 | $\alpha P_{96}$ |
| 7 | 7 | $\alpha P_{77}$ |
| 8 | 2 | $\alpha P_{28}$ |
| 9 | 5 | $\alpha P_{59}$ |
| | | $s'_1 = 1, s'_2 = 2, s'_3 = 3, s'_4 = 5, s'_5 = 7, s'_6 = 9$ |

$$\alpha = \frac{1}{\sum_{j=1}^{N'} P_{s_j,j}} \quad \text{Equation 12}$$

Next, the geometric calibration apparatus creates correspondences between phantom markers determined based on the extracted samples among the plurality of phantom markers and points determined based on the extracted samples among the detected points, and transforms the correspondences to obtain a candidate projection matrix $\hat{A}$ at S560. In some embodiments, the geometric calibration apparatus may obtain the candidate projection matrix $\hat{A}$ by designating $i(k)=s_{s'_k}$, $j(k)=s'_k$ (k=1, ..., 6) using the extracted samples, creating six correspondences $p_{i(k)} \leftrightarrow q'_{j(k)}$, and transforming the correspondences at S560. For example, the geometric calibration apparatus may create the correspondences as shown in Table 4 based on the example of Table 3. In some embodiments, as described above, the geometric calibration apparatus may apply DLT to the correspondences to obtain the projection matrix $\hat{A}$.

TABLE 4

| k | $p_{i(k)}$ | $q'_{j(k)}$ |
|---|---|---|
| 1 | $p_6$ | $q'_1$ |
| 2 | $p_3$ | $q'_2$ |
| 3 | $p_8$ | $q'_3$ |
| 4 | $p_4$ | $q'_5$ |
| 5 | $p_7$ | $q'_7$ |
| 6 | $p_5$ | $q'_9$ |

The geometric calibration apparatus calculates points $\hat{q}_i$ into which the markers $p_i$ are transformed by the candidate projection matrix $\hat{A}$, and calculates a difference $d(\hat{Q}, Q')$ between a set of transformed points $\hat{Q}=\{\hat{q}_1, \ldots, \hat{q}_M\}$ and a set of the detected points $Q'=\{q'_1, \ldots, q'_{N'}\}$ at S570. The geometric calibration apparatus may calculate the difference between the two sets by various techniques. In some embodiments, as shown in FIG. 8, the geometric calibration apparatus may obtain a minimum-weight perfect matching for a bipartite graph G in which the sets $\hat{Q}$ and $Q'$ are set as vertex sets and an edge $(\hat{q}_i, q'_j)$ between a vertex of the set $\hat{Q}$ and a vertex of the set $Q'$ has a weight $w_{ij}=\|\hat{q}_i-q'_j\|^2$, and calculate a sum of weights obtained by the minimum-weight perfect matching as the difference $d(\hat{Q},Q')$.

If the calculated difference $d((\hat{Q},Q')$ is less than or equal to a threshold ($d \le d_0$) at S580, the geometric calibration apparatus designates the candidate projection matrix $\hat{A}$ as the projection matrix A at S590. If the calculated difference $d(\hat{Q},Q')$ is greater than the threshold ($d > d_0$) at S580, the geometric calibration apparatus may discard the candidate projection matrix $\hat{A}$ and repeat the process from S540.

As described above, according to some embodiments, the geometric calibration phantom can be designed with almost no constraints, and additional information other than the phantom design is not required during geometric calibration. Accordingly, the user can arbitrarily dispose the phantom markers on the space as needed. According to some embodiments, the geometric calibration phantom can be designed with only one type of phantom markers, without needing, for example, to adopt different sizes to allow the phantom markers to be distinguished from each other. According to some embodiments, the geometric calibration can be achieved by using only the phantom marker position information without needing to know approximate information about the imaging directions in advance.

In some embodiments, the phantom design and fabrication, and training of the learning model can be performed only once for each phantom, as a pre-work for the geometric calibration. Based on the phantom and the learning model, the geometric calibration can be performed for each X-ray image acquired by a computer tomography device.

Hereinafter, an example computing device for implementing a learning apparatus or a geometric calibration apparatus according to various embodiment of the present invention is described with reference to FIG. 9.

Figure 9:
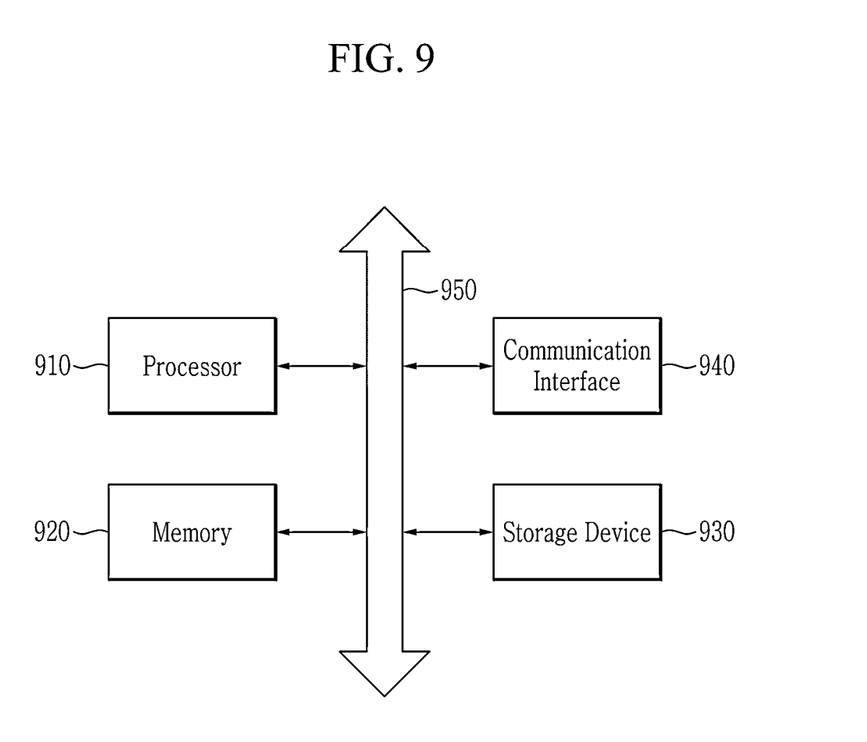
FIG. 9 is a drawing showing an example of a computing device according to an embodiment of the present invention.

FIG. 9 is a drawing showing an example of a computing device according to an embodiment of the present invention.

Referring to FIG. 9, a computing device includes a processor 910, a memory 920, a storage device 930, a communication interface 940, and a bus 950. The computing device may further include other general components.

The processor 910 controls an overall operation of each component of the computing device. The processor 910 may be implemented with at least one of various processing units such as a central processing unit (CPU), an application processor (AP), a microprocessor unit (MPU), a micro controller unit (MCU), and a graphic processing unit (GPU), or may be implemented with parallel processing units. In addition, the processor 910 may perform operations on a program for executing the above-described training data generation method, learning method, or geometric calibration method.

The memory 920 stores various data, instructions, and/or information. The memory 920 may load a computer program from the storage device 930 to execute the above-described training data generation method, learning method, or geometric calibration method. The storage device 930 may non-temporarily store a program. The storage device 930 may be implemented as a non-volatile memory.

The communication interface 940 supports wired or wireless Internet communication of the computing device. In addition, the communication interface 940 may support various communication methods other than Internet communication.

The bus 950 provides a communication function between the components of the computing device. The bus 950 may be implemented as various types of buses, such as an address bus, a data bus, and a control bus.

The computer program may include instructions for causing the processor 910 to execute the training data generation method, the learning method, or the geometric calibration method when loaded into the memory 920. That is, the processor 910 may perform the training data generation method, the learning method, or the geometric calibration method by executing the instructions.

In some embodiments, the computer program may include one or more instructions of detecting a plurality of first points from a plurality of projection regions, respectively, a plurality of first markers disposed on a phantom being projected onto the projection regions in two dimensions by a computer tomography device, calculating an output vector representing a probability distribution that gives a probability with which each of the first points is a projection of each of the first markers, by inputting data corresponding to each of the first points to a learning model, extracting a predetermined number of first samples based on the probability distribution, obtaining a candidate projection matrix by transforming correspondences between second markers determined based on the first samples among the first markers and second points determined based on the first samples among the plurality of first points, calculating third points into which the first markers are transformed by the candidate projection matrix, calculating a difference between a first set of the third points and a second set of the first points, and designating the candidate projection matrix as a projection matrix in response to the difference being less than or equal to a threshold.

In some embodiments, the computer program may include one or more instructions of generating training data that have, as input data, data corresponding to fourth points into which the first markers are respectively transformed by a randomly-generated projection matrix and have, as correct answer labels, values indicating classification of the first markers.

In some embodiments, a computer program may include one or more instructions for training the learning model using the training data.

In some embodiments, the computer program may include one or more instructions of detecting a plurality of points $q'_j$ ($j=1, \ldots, N'$) from a plurality of projection regions, respectively, a plurality of first markers disposed on a phantom being projected onto the projection regions in two dimensions by the computer tomography device, calculating an output vector $y_j=(P_{1j}, \ldots, P_{Mj})$ having, as elements, a probability $P_{ij}$ ($i=1, \ldots, M$) with which the $q'_j$ is a projection of each of the first markers, by inputting data corresponding to the $q'_j$ to a learning model, extracting samples $s'_k$ ($k=1, \ldots, 6$) from a set $\Omega'=\{1, \ldots, N'\}$ based on the $y_j$, obtaining a candidate projection matrix by transforming correspondences between second markers determined based on the samples $s'_k$ among the first markers and points determined based on the samples $s'_k$ among the $q'_j$, calculating points $\hat{q}_i$ into which the first markers are transformed by the candidate projection matrix, calculating a difference $d(\hat{Q}, Q')$ between a set $\hat{Q}=\{\hat{q}_1, \ldots, \hat{q}_M\}$ of the $\hat{q}_i$ and a set $Q'=\{q'_1, \ldots, q'_{N'}\}$ of the $q'_j$, and designating the candidate projection matrix as a projection matrix in response to the $d(\hat{Q}, Q')$ being less than or equal to a threshold.

The training data generation method, the learning method or the geometric calibration method according to various embodiments may be implemented as a computer-readable program on a computer-readable medium. In one embodiment, the computer-readable medium may include a removable recording medium or a fixed recording medium. In another embodiment, the computer-readable program recorded on the computer-readable medium may be transmitted to another computing device via a network such as the Internet and installed in another computing device, so that the computer program can be executed by another computing device.

While this invention has been described in connection with what is presently considered to be practical embodiments, it is to be understood that the invention is not limited to the disclosed embodiments. On the contrary, it is intended to cover various modifications and equivalent arrangements included within the spirit and scope of the appended claims.

What is claimed is:

1. A geometric calibration apparatus comprising:
   a memory configured to store one or more instructions; and
   a processor configured to, by executing the one or more instructions:
   detect a plurality of first points from a plurality of projection regions, respectively, a plurality of first markers disposed on a phantom being projected onto the projection regions in two dimensions by a computer tomography device;
   calculate an output vector representing a probability distribution that gives a probability with which each of the first points is a projection of each of the first markers, by inputting data corresponding to each of the first points to a learning model;
   extract a predetermined number of first samples based on the probability distribution;
   obtain a candidate projection matrix by transforming correspondences between second markers determined based on the first samples among the first markers and second points determined based on the first samples among the first points;

calculate third points into which the first markers are transformed by the candidate projection matrix;

calculate a difference between a first set of the third points and a second set of the first points; and designate the candidate projection matrix as a projection matrix in response to the difference being less than or equal to a threshold.

2. The geometric calibration apparatus of claim 1, wherein the processor is configured to transform each of the first points into a histogram, and wherein the data corresponding to each of the first points may be data obtained by being transformed into the histogram.

3. The geometric calibration apparatus of claim 1, wherein the processor is configured to extract the first samples by applying weighted random sampling to the probability distribution.

4. The geometric calibration apparatus of claim 1, wherein the processor is configured to:

extract a plurality of second samples for the first points, respectively, from a third set including indices of the first markers; and extract the first samples from a fourth set including indices of the first points such that a probability with which each element of the fourth set is extracted is a normalized value of a probability with which a first point corresponding to said each element among the first points is a projection of a marker at a second sample for the first point among the second samples.

5. The geometric calibration apparatus of claim 4, wherein the processor is configured to extract the first samples and the second samples using a weighted random sampling technique.

6. The geometric calibration apparatus of claim 4, wherein the second markers are markers that have, as indices, second samples corresponding to the first samples among the second samples, among the first markers, and wherein the second points are points having the first samples as indices among the first points.

7. The geometric calibration apparatus of claim 1, wherein the processor is configured to repeat a process of extracting the first samples, obtaining the candidate projection matrix, calculating the second points, and calculating the difference, in response to the difference being greater than the threshold.

8. The geometric calibration apparatus of claim 1, wherein the processor is configured to:

calculate a minimum-weight perfect matching for a bipartite graph in which the first set and the second set are set as vertex sets and an edge between a vertex of the first set and a vertex of the second set has a weight; and calculate a sum of weights obtained by the minimum-weight perfect matching as the difference.

9. The geometric calibration apparatus of claim 1, wherein the learning model is a model that has been trained by using training data that have, as input data, data corresponding to fourth points into which the first markers are respectively transformed by a randomly-generated projection matrix and have, as correct answer labels, values indicating classification of the first markers.

10. The geometric calibration apparatus of claim 9, wherein the data corresponding to the fourth points are data obtained by transforming the fourth points into a histogram.

11. The geometric calibration apparatus of claim 1, wherein the processor is configured to apply direct linear transformation to the correspondences to obtain the candidate projection matrix.

12. A geometric calibration method of a computer tomography device, the method comprising:

detecting a plurality of points $q'_j(j=1, \ldots, N')$ from a plurality of projection regions, respectively, a plurality of first markers disposed on a phantom being projected onto the projection regions in two dimensions by the computer tomography device;

calculating an output vector $y_j=(P_{1j}, \ldots, P_{Mj})$ having, as elements, a probability $P_{ij}(i=1, \ldots, M)$ with which the $q'_j$ is a projection of each of the first markers, by inputting data corresponding to the $q'_j$ to a learning model;

extracting samples $s'_k(k=1, \ldots, 6)$ from a set $\Omega'=\{1, \ldots, N'\}$ based on the $y_j$;

obtaining a candidate projection matrix by transforming correspondences between second markers determined based on the samples $s'_k$ among the first markers and points determined based on the samples $s'_k$ among the $q'_j$;

calculating points $\hat{q}_i$ into which the first markers are transformed by the candidate projection matrix;

calculating a difference $d(\hat{Q}, Q')$ between a set $\hat{Q}=\{\hat{q}_1, \ldots, \hat{q}_M\}$ of the $\hat{q}_i$ and a set $Q'=\{q'_1, \ldots, q'_{N'}\}$ of the $q'_j$; and designating the candidate projection matrix as a projection matrix in response to the $d(\hat{Q}, Q')$ being less than or equal to a threshold.

13. The method of claim 12, further comprising transforming the $q'_j$ into a histogram, wherein the data corresponding to the $q'_j$ are data obtained by being transformed into the histogram.

14. The method of claim 12, wherein extracting the $s'_k$ comprises:

extracting samples $s_j \in \Omega$ from a set $\Omega=\{1, \ldots, M\}$ such that a probability with which each element i of the set $\Omega$ is extracted for a given j is the $P_{ij}$;

normalizing a probability $P_{s_j,j}$ at the $s_j$ into $\alpha P_{s_j,j}$; and extracting the $s'_k$ such that a probability with which each element j of the $\Omega'$ is extracted from the $\Omega'$ is $\alpha P_{s_j,j}$.

15. The method of claim 14, wherein the $\alpha$ is a reciprocal of a sum of the $P_{s_j,j}$ at the $s_j$.

16. The method of claim 12, wherein calculating the $d(\hat{Q}, Q')$ comprises:

calculating a minimum-weight perfect matching for a bipartite graph in which the $\hat{Q}$ and the $Q'$ are set as vertex sets and an edge between a vertex $\hat{q}_i$ of $\hat{Q}$ and a vertex of $q'_j$ of $Q'$ has a weight $w_{ij}=\|\hat{q}_i-q'_j\|^2$; and calculating a sum of weights obtained by the minimum-weight perfect matching as the $d(\hat{Q}, Q')$.

17. The method of claim 12, further comprising, in response to the $d(\hat{Q}, Q')$ being greater than the threshold, repeating extracting the $s'_k$, obtaining the candidate projection matrix, calculating the $\hat{q}_i$, and calculating the $d(\hat{Q}, Q')$.

18. A computer program executed by a computing device and stored in a non-transitory recording medium, the computer program causing the computing device to execute:

detecting a plurality of first points from a plurality of projection regions, respectively, a plurality of first markers disposed on a phantom being projected onto the projection regions in two dimensions by a computer tomography device;

calculating an output vector representing a probability distribution that gives a probability with which each of the first points is a projection of each of the first markers, by inputting data corresponding to each of the first points to a learning model;

extracting a predetermined number of first samples based on the probability distribution;

obtaining a candidate projection matrix by transforming correspondences between second markers determined based on the first samples among the first markers and second points determined based on the first samples among the plurality of first points;

calculating third points into which the first markers are transformed by the candidate projection matrix;

calculating a difference between a first set of the third points and a second set of the first points; and designating the candidate projection matrix as a projection matrix in response to the difference being less than or equal to a threshold.

* * * * *